United States Patent
Mehtali et al.

(10) Patent No.: US 6,399,587 B1
(45) Date of Patent: Jun. 4, 2002

(54) RECOMBINANT ADENOVIRAL VECTORS COMPRISING A SPLICING SEQUENCE

(75) Inventors: Majid Mehtali, Graffenstaden; Pierre Leroy, Strasbourg, both of (FR); Anne-Isabelle Michou, Vienna (AT)

(73) Assignee: Transgene S.A., Strasbourg (FR)

( * ) Notice: Subject to any disclaimer, the term of this patent is extended or adjusted under 35 U.S.C. 154(b) by 0 days.

(21) Appl. No.: 09/445,093

(22) PCT Filed: Jun. 2, 1998

(86) PCT No.: PCT/FR98/01105

§ 371 (c)(1),
(2), (4) Date: Dec. 2, 1999

(87) PCT Pub. No.: WO98/55639

PCT Pub. Date: Dec. 10, 1998

(30) Foreign Application Priority Data

Jun. 2, 1997 (FR) ............................................. 97 06757

(51) Int. Cl.[7] .......................... A61K 48/00; A61K 35/00; C12N 15/63; C12N 15/85; C12N 15/86; C07H 21/04

(52) U.S. Cl. ...................... 514/44; 435/320.1; 435/325; 435/455; 424/93.2; 536/23.1; 536/24.1

(58) Field of Search ......................... 514/44; 435/320.1, 435/325, 455; 536/24.1, 23.1; 424/93.2

(56) References Cited

U.S. PATENT DOCUMENTS 5,518,913 A  5/1996  Massie et al. ........... 435/235.1
5,935,935 A  * 8/1999  Connelly et al. ............... 514/4

FOREIGN PATENT DOCUMENTS

| EP | 0 732 405 A1 | 9/1996 |
| WO | 94/12649 | 6/1994 |
| WO | 94/24971 | 12/1994 |
| WO | 95/16772 | 6/1995 |
| WO | 96/33280 | 10/1996 |
| WO | 97/04119 | 2/1997 |

OTHER PUBLICATIONS

Brondyk et al. Promega Notes 1994; 49:7–11.*
Levine et al. Mole Med Today Apr. 1999; 5:165–171.*
Orkin et al. NIH Report, Dec. 1995.*
Robbins et al. Pharmacol Ther 1998;80:35–47.*
Zhang et al. Exp Opin Invest Drugs 1995; 487–514.*
AR Buchman et al., Molecular and Cellular Biology, "Comparison of Intron–Dependent and Intron–Independent Gene Expression," Oct. 1988, vol. 8, No. 10, pp. 4395–4405.*
Axelrod J.H., et al: "Phenotypic correction of factor IX deficiency in skin fibroblasts of hemophilic dogs" Proc. Natl. Acad. Sci. USA, vol. 87 pp. 5173–5177, Jul. 1990.

Bajaj S. Paul, et al: "A Monoclonal Antibody to Factor IX That Inhibits the Factor VIII:Ca Potentiation of Factor X Activation" The Journal of Biological Chemistry, vol. 260, No. 21, pp. 11574–11580, Sep. 25, 1985.
Brinster Ralph L., et al: "Intron increase transcriptional efficiency in transgenic mice" Proc. Natl. Acad. Sci. USA, vol. 85 pp. 836–840, Feb. 1988.
Byrn Randal A., et al: "Biological properties of a CD4 immunoadhesin" Nature, vol. 344 pp. 667–670, Apr. 12, 1990.
Buchacher Andrea, et al: "Human monoclonal Antibodies against gp41 and gp120 as Potential Agent for Passive Immunization" Vaccines 92, copyright 1992, pp. 191–105.
Buchman Andrew R., et al: "Comparison of Intron–Dependent and Intron–Independent Gene Expression" Molecular and Cellular Biology, vol 8 pp. 4395–4405, Oct. 1988.
Capon Daniel J., et al: "Designing CD4 immunoadnesins for AIDS therapy" Nature vol. 337, Feb. 9, 1989, pp. 525–531.
Chartier C., et al: "Efficient Generation of Recombinant Adenovirus Vectors by Homologous Recombination in *Escherichia coli*" Journal of Virology, vol. 70, No. 7 pp. 4805–4810, Jul. 1996.
Chen Ling, et al: "Breast Cancer Selective Gene Expression and Therapy Mediated by Recombinant Adenoviruses Containing the DF3/MUC1 Promoter" The American Society for Clinical Investigation, Inc. , vol. 96 pp. 2775–2782, Dec. 1995.
Connelly Sheila, et al: "High–Level Tissue–Specific Expression of Functional Human Factor VII in Mice" Human Gene Therapy 7:183–195, Jan. 20, 1996, pp. 183–195, XP–002055414.
Ensinger Marcia J., et al: "Selection and Preliminary Characterization of Temperature–Sensitive Mutants of Type 5 Adenovirus" Journal of Virology, pp. 328–339, Sep. 1972.
Evans James P., et al: "Molecular cloning of a cDNA Encoding Canine Factor IX" Blood, vol. 74, No. 1 (Jul.) 1989, pp. 207–212.

(List continued on next page.)

*Primary Examiner*—James Ketter
*Assistant Examiner*—J Janice Li
(74) *Attorney, Agent, or Firm*—Burns, Doane, Swecker & Mathis, L.L.P.

(57) ABSTRACT

The invention concerns a recombinant adenoviral vector driving from an adenovirus genome at least by deleting all or part of the E1 region, the adenoviral vector comprising an expression cassette of a gene of interest placed under the control of elements necessary for its expression in a host cell or a host organism, the elements required for its expression including at least a splicing sequence. The invention is characterized in that the splicing sequence is derived from a eukaryotic nuclear gene selected among the ovalbumen genes, β or β-globine, collagen and factor VIII of mammals or a synthetic splicing sequence. The invention also concerns a host cell and an infectious viral particle comprising such a vector, a method for preparing such a particle and their therapeutic or prophylactic use. The invention further concerns a pharmaceutical composition containing the adenoviral vector, the host cell or the viral particle.

13 Claims, 1 Drawing Sheet

OTHER PUBLICATIONS

Pelgner P.L., et al: "Cationic Liposome Mediated Transfection" Proc. West. Pharmacol. Soc. 32:115–121 (1989), pp. 115–121.

Gooding Linda R., et al: "Molecular Mechanisms by Which Adenoviruses Counteract Antiviral Immune Defenses" Immunology, vol. 10, Issue 1, pp. 53–71.

Graham F.L., et al: "Characteristics of a Human cell Line Transformed by DNA from Human Adenovirus Type 5" J. Gen. Virol. (1977), 36, pp. 59–72.

Green S. et al: "A Versatile in vivo and in vitro eukaryotic expression vector for protein engineering" Nucleic Acids Research, vol. 16, No. 1, 1988, p. 369.

Promega Catalogue 1996, p. 213, Vecteur pCI, XP002084598.

Hannahan, Douglas: "Studies on Transformation of *Escherichia coli* with Plasmids" J. Mol. Biol. (1983) 166, pp. 557–580.

Harris Jonathan D., et al: "Gene therapy for cancer using tumour–specific prodrug activation" Gene Therapy (1994) 1, pp. 170–175.

Hodgson Clague P., et al: "Virosomes: Cationic Liposomes Enhance Retroviral Transduction" Nature Biotechnology, vol. 14, Mar. 1996, pp. 339–3442.

Huang Manley T.F., et al: "Intervening sequences increase efficiency of RNA 3' processing and accumulation of cytoplasmic RNA" Nucleic Acids Research, vol. 18, No. 4, pp. 937–947.

Jouvenne Patricia, et al: "Cloning, physical mapping and cross–hybridization of the canine adeovirus types 1 and 2 genomes" Gene, 60 (1987) pp. 21–28.

Kanai, Fumihiko, et al: "In Vivo Gene Therapy for x–Fetoprotein–producing Hepatocellular Carcinoma by Adenovirus–mediated Transfer of cytosine Deaminase Gene[1]" Cancer Research 57, Feb. 1, 1997, pp. 461–465.

Karasuyama, Hajime, et al: "Autocrine Growth and Tumorigenicity of Interleukin 2–Dependent Helper T Cells Transfected with IL–2 Gene" J. Exp. Med., vol. 169, Jan. 1989, pp. 13–25.

Karasuyama, H. et al: "Establishment of mouse cell lines which constitutively secrete large quantities of interleukin 2,3, 4 or 5, using modified cDNA expression vectors" Eur. Journal of Immunol., vol. 18, No. 1, Jan. 1, 1988, pp. 97–104 XP000565567.

Kurachi, Kotoku, et al: "Sequence of the cDNA and Gene for Angiogenin, a Human Angiogenesis Factor" Biochemistry 19985, 24, pp. 5494–5499.

Kurachi, Sumiko, et al: "Role of Introl 1 in Expression of the Human Factor IX Gene" The Journal of Biological Chemistry, vol. 270, No. 10, Mar. 10, 1995 pp. 5276–5281, XP002055415.

Lozier Jay, et al: "Gene Therapy and the Hemophilias" JAMA, Jan. 5, 1994, vol. 271, No. 1, pp 47–51.

Lusky, M. et al: "In Vitro and In Vivo Biology of Recombinant Adenovirus Vectors with E1, E1/E2A, or E1/E4 Deleted" Journal of Virology, Mar. 1988, pp. 2022–2032.

Mittal Suresh K., et al: "Development of a bovine adenovirus type 3–based expression vector" Journal of General Virology (1994, 76, pp. 93–102.

Miyanohara, Atsushi, et al: "Direct Gene Transfer to the Liver with Herpes Simplex Virus Type 1 Vectors: Transient Production of Physiologically Relevant Levels of Circulating Factor IX" The New Biologist, vol. 4, No. 3 (Mar.) 1992, pp. 238–246.

Reich Nancy C., et al: "Monoclonal Antibodies Which Recognize Native and Denatured Forms of the Adenovirus DNA–Binding Protein" Virology 128, (1983), pp. 480–484.

Remy, Jean–Serge, et al: "Gene Transfer with a Series of Lipophilic DNA–Binding Molecules" Bioconjungate Chem. 1994, 5, pp. 647–654.

Roman M., et al: "Circulating Human or Canine Factor IX from Retrovirally Transduced Primary Myoblasts and Established Myoblast Cell Lines Grafted into Murine Skeletal Muscle" Somatic Cell and Molecular Genetics, vol. 18, No. 3, 1992, pp. 247–258.

Spibey, N., et al: "Molecular Cloning and Restriction Endonuclease Mapping of Two Strains of Canine Adenovirus Type 2" J. Gen Virol. (1989), 70, pp. 165–172.

Schrewe, Heinrich, et al: "Cloning of the complete Gene for Carcinoembryonic Antigen Analysis of Its Promoter Indicates a Region Conveying Cell Type–Specific Expression" Molecular and Cellular Biology, Jun. 1990, pp. 2738–2748.

Takebe, Yutake, et al: "SRx Promoter: an Efficient and Versatile Mammalian cDNA Expression System Composed of the Simiam Virus 40 Early Promoter and the R–U5 Segment of Human T–Cell Leukemia Virus Type 1 Long Terminal Repeat" Molecular and Cellular Biology, Jan. 1988, pp. 466–472.

Taniguchi, Tadatsugu, et al: "Structure and expression of a cloned CDNA for human interleukin–2" Nature vol. 302, Mar., 24, 1983, pp. 305–310.

Traunecker, Andre, et al: "Soluble CD4 molecules neutralize human immunodeficiency virus type 1" Nature vol. 331, Jan. 7, 1988, pp. 84–86.

Vile Richard G., et al: "Use of Tissue–Specific Expression of the Herpes Simplex Virus Thymidine Kinase Gene to Inhibit Growth of Established Murine Melanomas following Direct Intratumoral Injection of DNA" Cancer Research 53, Sep. 1, 1993, pp. 3860–3864.

Weinberg David H., et al: "A cell line that supports the growth of a defective early region 4 deletion mutant of human adenovirus type 2" Proc. Natl. Acad. Sci. USA, vol. 80, Sep. 1983, pp. 5383–5386.

Zakharchuk, A. N., et al: "Physical mapping and homology studies of egg drop syndrome" Arch Virol (1993) 128: pp. 171–176.

* cited by examiner

RECOMBINANT ADENOVIRAL VECTORS COMPRISING A SPLICING SEQUENCE

The present invention relates to adenoviral vectors which contain a cassette for expressing a gene of interest which is placed under the control of the elements which are required for expressing it, and which comprise splicing sequences. The presence of these sequences markedly increases the expression of the therapeutic gene in a host cell or organism. The invention also relates to the cells and the infectious viral particles which contain these novel vectors and to a method for preparing them. The invention is of especial interest from the point of view of gene therapy, in particular gene therapy in man.

BACKGROUND OF THE INVENTION

Gene therapy is defined as being the transfer of genetic information into a host cell or organism. The first protocol applied to man was initiated, in the United States in September 1990, on a patient who was genetically immunodeficient due to a mutation which affected the gene encoding Adenine Deaminase (ADA). The relative success of this first experiment encouraged the development of this technology for a variety of diseases including both genetic (with the aim of correcting the malfunction of a defective gene) and acquired (infectious diseases, cancers, etc.) diseases. At the present time, the majority of protocols use retroviral vectors for transferring the therapeutic gene into the cells to be treated and expressing it in the cells. However, in addition to their restricted cloning capacity, retroviral vectors suffer from two major drawbacks which limit their systematic use: on the one hand, they mainly infect dividing cells and on the other hand, because they integrate randomly into the genome of the host cell, the risk of insertional mutagenesis is not insignificant. For this reason, a large number of scientific groups has been endeavoring to develop other types of vector, including adenoviruses.

Adenoviruses have been demonstrated to be present in a large number of animal species; they are not very pathogenic, they do not integrate and they replicate equally well in dividing and quiescent cells. Furthermore, they have a wide host spectrum and are able to infect a large number of cell types, in particular epithelial and endothelial cells, myocytes, hepatocytes, nerve cells and synoviocytes. In addition, they possess a natural tropism for the airways. These specific properties make adenoviruses vectors of choice for a large number of therapeutic and even vaccinal applications.

As a general rule, the adenoviral genome consists of a linear, double-stranded DNA molecule of approximately 36 kb in size which carries more than 30 genes encoding the viral proteins and, at its ends, two inverted repeats (designated ITR, standing for Inverted Terminal Repeat) and the encapsidation region. The early genes, which are required for replicating the virus, are divided up into 4 regions (E1 to E4, E for early) which are dispersed within the genome and which contain 6 transcriptional units provided with their own promoter. The late genes (L1 to L5, L for late), which encode the structural proteins, partially cover the early transcription units and are for the most part transcribed from the major late promoter MLP (see FIG. 1).

The adenoviral vectors which are currently employed in gene therapy protocols are so-called first-generation vectors, which vectors lack the major part of the E1 region, which is essential for replication, in order to avoid the vectors being disseminated in the environment and in the host organism. Deletion of the non-essential E3 region increases the cloning capacity of the vectors. The genes of interest are introduced into the viral DNA in place of one or other of the deleted regions. These replication-defective viruses can be propagated in a cell line which complements the E1 function. Use is commonly made of the 293 cell line, which was developed from human embryonic kidney cells (Graham et al., 1977, J. Gen. Virol. 36, 59–72). The deletion of the non-essential E3 region does not require any specific complementation. Even if the feasibility of transferring genes using these first-generation vectors is now well established, there is still the question of whether or not they are harmless. As well as the safety aspects (risk of generating replication-competent particles), the problem of their toxicity also arises. Thus, the first clinical trials provided evidence of the induction of inflammatory responses which were due to the expression of the viral genes in the host and which opposed the persistence of the transduced cells and expression of the transgene. These drawbacks linked to stimulation of the host immune system by the adenoviral epitopes have justified constructing new-generation viruses.

The design of an adenoviral vector is on the one hand based on the viral skeleton and on the other hand based on the cassette for expressing the therapeutic gene, with this gene being combined with regulatory elements which enable it to be expressed optimally in the host cell. With regard to the first point, the second-generation adenoviral vectors retain the in cis ITR regions and encapsidation sequences and contain substantial internal deletions which are aimed at suppressing most of the viral genes whose expression in vivo is undesirable (see international application WO94/28152). Their propagation is ensured by using a helper virus or cell lines which complement the defective functions. For example, a cell line which is derived from 293 and which expresses the adenoviral sequences encoding the essential E4 proteins will be used for complementing a second-generation vector whose genomic skeleton has been deleted for the E1, E3 and E4 regions.

As far as the expression cassette is concerned, this generally comprises a 5' promoter region which directs transcription of the gene which follows it and possibly a 3' polyadenylation (polyA) sequence which contributes, in particular, to stabilizing the transcribed messenger. Additional elements may improve expression under certain circumstances. The positive effect of intron sequences on gene expression has already been reported in vitro (Buchman and Berg, 1988, Mol. Cell. Biol. 8, 4395–4405; Huang and Gorman, 1990, Nucleic Acid Res. 18, 937–947), in vivo in transgenic animals (Brinster et al., 1988, Proc Natl. Acad. Sci. USA 85, 836–840) and, more recently, in the context of a first-generation adenoviral vector (Connelly et al., 1996, Human Gene Therapy 7, 183–195). This document shows that mice which have been treated with an adenovirus which has been deleted for the E1 and E3 regions and which is expressing human factor VIII produce levels of serum factor VIII which are 3 to 13 times higher when the complementary FVIII DNA contains splicing sequences.

BRIEF SUMMARY OF THE INVENTION

The object of the present invention is to make adenoviral vectors available to the public which are more efficient from the point of view of expressing the therapeutic gene and which thereby make it possible to reduce the vector doses and to amplify the therapeutic effect. It has now been demonstrated that the presence of splicing sequences within the gene of interest is beneficial, if not essential, for obtaining expression of the gene. This observation is particularly true within the context of a second-generation adenoviral vector, where the levels at which the canine factor IX (FIX) and human interleukin 2 (IL-2) therapeutic genes are expressed are amplified by a factor of 20 to 150 when the expression cassette includes the said splicing sequences. The amplification factor remains significant (2 to 3) when a first-generation vector is used. This substantial improvement in gene expression is unexpected and could not be deduced from the state of the art.

For this reason, the present invention relates to an adenoviral vector which is derived from an adenovirus genome by deleting at least all or part of the E1 region, with the said adenoviral vector containing a cassette for expressing a gene of interest which is placed under the control of the elements which are required for expressing it in a host host cell or organism, with the said elements which are required for the expression comprising at least one splicing sequence, characterized in that the said splicing sequence is derived from a eukaryotic nuclear gene which is selected from the mammalian factor VIII, collagen, α- or β-globin and ovalbumin genes, or from a synthetic splicing sequence.

DETAILED DESCRIPTION OF THE INVENTION

Figure 1:
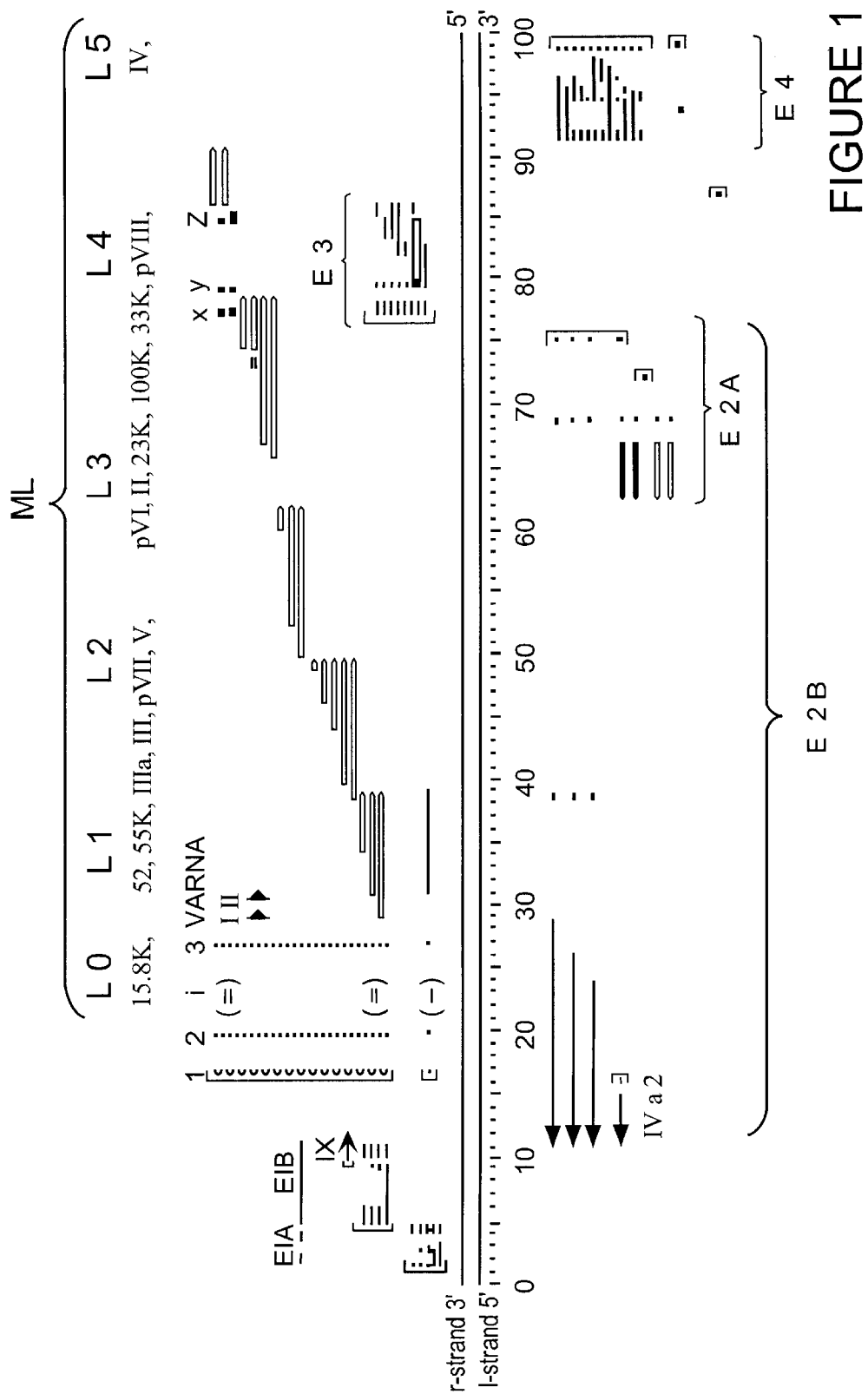
FIG. 1 is a diagram of the genome of the human type 5 adenovirus (depicted in 0 to 100 arbitrary units) showing the locations of the different genes.

Within the meaning of the present invention, the term adenoviral vector refers to an adenovirus which is defective for replication (incapable of replicating autonomously in a host cell) in the absence of any complementation. As compared with the parental adenovirus, the vector according to the invention is modified at least in the E1 region as the result of the total or partial deletion of this latter region. According to one advantageous embodiment, at least one of the regions selected from E2, E4, L1, L2, L3, L4 and L5 is also nonfunctional. The nonfunctionality can be obtained by totally or partially deleting one or more of the regions concerned or by introducing (a) mutation(s) (deletion, addition and/or substitution of one or more nucleotides) which render(s) the mutated adenoviral gene defective. These modifications may affect the coding sequences or the noncoding sequences, in particular the promoter regions, of the viral genome. The temperature-sensitive mutation affecting the DBP (DNA-binding protein) gene of the E2A region (Ensinger et al., 1972, J. Virol. 10, 328–339) may be mentioned for the purpose of illustrating these embodiments. A partial deletion can consist in eliminating the E4 region apart from the sequences which encode open reading frames (ORFs) 6 and 7, which do not require complementation of the E4 function (Ketner et al., 1989, Nucleic Acids Res. 17, 3037–3048). A total deletion of E4 includes the complete transcriptional unit.

It is pointed out that an adenoviral vector according to the invention retains the in cis regions of the adenoviral genome, namely the inverted terminal repeats (ITRs) and the encapsidation region. Their length and nucleotide sequence can vary from one serotype to another. However, they can be easily isolated on the basis of the data given in the literature. For information, the first 458 nucleotides (nt) of the type 5 adenovirus (Ad5) genome carry the 5' ITR and the encapsidation region, while the last 103 nt correspond to the 3' ITR. Advantageously, the adenoviral vector according to the invention also comprises the sequences encoding the pIX protein unless they are complemented by the producer cell line. Furthermore, the vector can also lack all or part of the E3 region. Another alternative consists in retaining the E3 sequences which encode the polypeptides which make it possible to evade the host immune system, in particular the gp19k glycoprotein (Gooding et al., 1990, Critical Review of Immunology 10, 53–71). In the context of the present invention, it is possible to use the so-called second-generation vectors from the state of the art (see, for example, international applications WO94/28152 and WO97/04119).

An adenoviral vector according to invention can also be modified at the level of the sequences which encode the late proteins, such as the hexon, the penton or the fiber proteins, in order to modify the infectivity of the virion, for example for the purpose of targeting one particular cell type (see, for example, French application FR97 04747).

An adenoviral vector which is preferred in accordance with the invention is selected from the following vectors:
(1) adenoviral vector which lacks all or part of the E1 and E2 regions and, optionally, all or part of E3,
(2) adenoviral vector which lacks all or part of the E1 and E4 regions and, optionally, all or part of E3,
(3) adenoviral vector which lacks all or part of the E1 and E4 regions and, optionally, all or part of E3, and which contains a nonfunctional mutation in the E2 region, and
(4) adenoviral vector which lacks all or part of the E1, E2 and E4 regions and, optionally, all or part of E3.
(5) adenoviral vector which lacks all or part of the E1 region and, optionally, all or part of E3.

The origin of the adenoviral vector according to the invention can be varied both from the point of view of the species and from the point of view of the serotype. The adenoviral vector can be derived from the genome of an adenovirus of human, canine, avian, bovine, murine, ovine, porcine or simian origin or else from a hybrid which comprises adenoviral genome fragments of different origins. The CAV-1 or CAV-2 adenoviruses of canine origin, the DAV adenovirus of avian origin or the Bad type 3 adenovirus of bovine origin (Zakharchuk et al., Arch. Virol., 1993, 128: 171–176; Spibey and Cavanagh, J. Gen. Virol., 1989, 70: 165–172; Jouvenne et al., Gene, 1987, 60: 21–28; Mittal et al., J. Gen. Virol., 1995, 76: 93–102) may more particularly be mentioned. However, preference will be given to an adenoviral vector of human origin which is preferably derived from a serotype C adenovirus, in particular from a type 2 or type 5 serotype C adenovirus. Furthermore, the adenoviral vector according to the present invention can be generated in vitro in *Escherichia coli* (*E. coli*) by means of molecular-biology techniques or else by means of homologous recombination (see, for example, international application WO96/17070).

As has previously been pointed out, the adenoviral vector according to the invention is recombinant and contains at least one cassette for expressing a gene of interest which is placed under the control of the elements which are required for expressing it in a host cell or a host organism. Preferably, the expression cassette is inserted into the adenoviral vector according to the invention in place of one of the deleted regions, in particular the E1 region. When several expression cassettes are used, they can be inserted at the same site or at different sites in the viral genome and can use the same regulatory elements or different regulatory elements and can, where appropriate, be in opposite orientations with respect to each other in order to minimize interference phenomena at the level of gene expression.

The essential feature of at least one of the expression cassettes employed within the context of the present invention is that of comprising at least one splicing sequence. The term "splicing sequence" refers to a sequence which is as a rule active in splicing an intervening sequence (ivs) which is situated between two splicing points and which is present in a nuclear gene between two exons and absent from the corresponding messenger RNA (mRNA). The exons are the sequence segments which go to make up the MRNA. They can be coding or noncoding, with the noncoding exons being in particular those which are located at the 5' and 3' ends. The splicing points represent the borderline points between exon and ivs, with the donor point being at the beginning of the ivs and the acceptor point being at the end. The said splicing sequence comprises at least the sequences which are located directly 3' of the donor point and 5' of the splicing acceptor point and, where appropriate, a sequence of any size which separates them. The splicing sequence can also contain additional sequences at one or other of its two ends. Preference will be given to using noncoding exon sequences which are involved directly in the splicing process and comprise the sequences directly 5' of the donor point and 3' of the splicing donor point. This embodiment is preferably advantageous when using a gene of interest of the complementary DNA (cDNA type). The sequences which are directly involved in the splicing (splicing sites which cover the exon-ivs junction) are relatively well conserved in evolution and the consensuses are disclosed in most of the basic textbooks dealing with eukaryotic gene expression (for example in Watson et al., 1989, in Molecular Biology of the Gene, 4 ed, pp 683–742, Benjamin/Cummings Publishing Company Inc., Menlo Park, Calif.). In particular, the GT and AG sequences which are respectively situated downstream and upstream of the 5' (donor) and 3' (acceptor) splicing points are almost invariant.

It is known that a large number of eukaryotic genes consist of a succession of exons and introns. In the context of the present invention, use is made of splicing sequence which is derived from a nuclear gene which is transcribed by an RNA polymerase II and which is selected from the mammalian factor VIII, collagen, α- and β-globin and ovalbumin genes, or from a synthetic splicing sequence. The lengths and sequences of the splicing sequences which can be implemented in the present invention can differ widely. The splicing sequence can be a native splicing sequence as found in nature. It is also possible to use a splicing sequence which has been modified, in particular by deleting one or more sequences which are not active in the splicing process, with the aim of reducing its size or of removing repeat sequences, which can lead to recombination phenomena, or regulatory sequences which may disrupt the expression of the gene of interest. It is possible to envisage using a chimeric splicing sequence which is formed from sequences of varying origin. As an illustration of this aspect, the chimeric intron can be formed from the 5' and 3' parts of two different introns or be provided with a splicing donor site and/or a heterologous splicing acceptor site. It is also possible to use a synthetic splicing sequence which has been designed on the basis of the consensus splicing sites. A splicing sequence which is preferred in accordance with the invention is derived from the second intron of the rabbit β-globin gene (Green et al, 1988, Nucleic Acid Res. 16, 369; Karasuyama et al., 1988, Eur. J. Immunol. 18, 97–104; Karasuyama et al., 1989, J. Exp. Med. 169, 13–25), or from that found in the plasmid pCI (Promega Corp, pCI mammalian expression vector E1731), which sequence comprises the splicing donor site of intron 1 of the human β-globin gene as well as the branching point and the splicing acceptor site of the gene for a mouse immunoglobin.

An adenoviral vector according to the invention preferably comprises a splicing sequence which is homologous with, or identical to, all or part of the sequence depicted in sequence identifier IDS 1 or IDS 2. Homologous is understood as meaning an identity of sequence between the sequence used in the present invention and that reported in one or other of the IDSs of at least 70%, advantageously of at least 80%, preferably of at least 90% and, very preferably, of at least 95%. Sequence identity signifies 100% identity and "approximately as" denotes a sequence identity of at least 95%. A part comprises at least 17 continuous nt. An adenoviral vector according to the invention which comprises a splicing sequence which is approximately as depicted in sequence identifier IDS 1 or 2 is very particularly suitable.

In accordance with the aims pursued by the present invention, the expression cassette can contain one or more splicing sequences inserted into one or more genes of interest which are of the genomic, minigene (type obtained by mixing genomic and cDNA)or else cDNA (lacking introns) type and which are carried by the said cassette. The preferred site of insertion of the splicing sequence within the gene of interest is between the first exon and the second exon. When the gene of interest is of the cDNA type, preference will be given to using a splicing sequence which is provided with short exon sequences and which can be inserted 5' or 3' of the cDNA. The gene of interest can be homologous with, or heterologous to, the host cell and can encode an antisense RNA, a ribozyme or a polypeptide of interest which is located in the nucleus, in the cytoplasm or in the membrane or which is secreted. The polypeptide of interest can be a native polypeptide, as found in nature, a functional fragment, a mutant whose biological properties have been improved and/or modified, or else a chimera which is derived from fusing sequences of different origins. The gene of interest may be obtained by chemical synthesis or by cloning (screening a DNA library with appropriate probes, PCR, etc.) and can be modified by means of conventional molecular-biology techniques.

Within the context of the present invention, it can be advantageous to use a gene of interest which encodes a cytokine (α, β or γ interferon, interleukin (IL), in particular IL-2, IL-6, IL-10 or IL-12, a tumor necrosis factor (TNF), a colony-stimulating factor (GM-CSF, C-CSF, M-CSF, etc.), a cell receptor (in particular recognized by the HIV virus), a receptor ligand, a coagulation factor, a growth factor (FGF, standing for Fibroblast Growth factor, VEGF, standing for Vascular Endothelial Growth Factor, etc.), an enzyme (urease, renin, thrombin, metalloproteinase, NOS, standing for Nitric Oxide synthetase, SOD, catalase, etc.), an enzyme inibitor (α1-antitrypsin, antithrombin III, viral protease inhibitor, PAI-1, standing for plasminogen activator inhibitor, etc.), a class I or II major histocompatability complex antigen or a polypeptide which acts on the expression of the corresponding genes, a polypeptide which is able to inhibit a viral, bacterial or parasitic infection or its development, a polypeptide which reacts positively or negatively on apoptosis (Bax, Bcl2, BclX, etc.), a cytostatic agent (p21, p16, Rb etc.), an apolipoprotein (ApoAI, ApoAIV, ApoE, etc.), an angiogenesis inhibitor (angiostatin, endostatin, etc.), a marker (β-galactosidase, luciferase, etc.) or any other gene of interest which has a therapeutic effect on the targeted ailment.

More precisely, for the purpose of treating an hereditary malfunction, use will be made of a functional copy of the defective gene, for example a gene encoding factor VIII or factor IX within the context of A or B hemophilia, dystrophin within the context of Duchenne's and Becker's myopathies, insulin within the context of diabetes, and the CFTR (Cystic Fibrosis Transmembrane Conductance Regulator) protein within the context of cystic fibrosis. As regards inhibiting the initiation or progress of tumors or cancers, preference will be given to using a gene of interest which encodes an antisense RNA, a ribozyme, a cytotoxic product (herpes simplex 1 virus thymidine kinase (HSV-1-TK), ricin, cholera or diptheria toxin, expression product of the FCY1 and FUR1 yeast genes encoding uracil phosphoribosyl transferase and cytosine deaminase, etc.), an antibody, an inhibitor of cell division or transduction signals, an expression product of a tumor suppressor gene (p53, Rb, p73, etc.), a polypeptide which stimulates the immune system, a tumor-associated antigen (MUC-1, BRCA-1, early or late antigens (E6, E7, L1, L2, etc.), of an HPV papilloma virus, etc.), where appropriate in combination with a cytokine gene. Finally, use can be made, within the context of an anti-HIV therapy, of a gene which encodes an immunoprotected polypeptide, an antigen epitope, an antibody (2F5; Buchacher et al., 1992, Vaccines 92, 191–195), the extracellular domain of the CD4 receptor (sCD4; Traunecker et al., 1988, Nature 331, 84–86), an immunoadhesin (for example a CD4-IgG immunoglobulin hybrid; Capon et al., 1989, Nature 337, 525–531; Byrn et al., 1990, Nature 344, 677–670), an immunotoxin (for example fusion of the antibody 2F5 or the immunoadhesin CD4-2F5 to angiogenin; Kurachi et al., 1985, Biochemistry 24, 5494–5499), a transdominant variant, a cytotoxic product such as one of those mentioned above, or else an α or β IFN.

Furthermore, the expression cassette which is used in the present invention can also comprise a selection gene which enables the transfected cells to be selected or identified. Mention may be made of the neo gene (encoding neomycin phosphotransferase), which confers resistance to the antibiotic G418, the dhfr (Dihydrofolate Reductase) gene, the CAT (Chloramphenicol Acetyl transferase) gene, the pac (Puromycin Acetyl Transferase) gene or else the gpt (Xanthine Guanine Phosphoribosyl Transferase) gene. Generally speaking, the selection genes are known to the skilled person.

The phrase "elements which are required for expression" denotes the genetic elements which enable a gene of interest to be transcribed into RNA and an mRNA to be translated into polypeptide. Of these elements, the promoter is of particular importance. It can be isolated from any gene of eukaryotic or even viral origin and can be constitutive or regulatable. Alternatively, the promoter can be the natural promoter of the gene in question. Furthermore, it can be modified so as to improve the promoter activity, to suppress a region which inhibits transcription, to render a constitutive promoter regulatable or vice versa, to introduce a restriction site, etc. Examples of promoters which may be mentioned are the CMV (Cytomegalovirus) and RSV (Rous Sarcoma Virus) viral promoters, the promoter of the HSV-1 virus TK gene, the SV40 (Simian Virus 40) virus early promoter, the adenoviral promoter of an early or late (E1A, MLP, etc.) gene, or else the eukaryotic promoters of the PGK (Phospho Glycerate kinase), MT (metallothionein), α1-antitrypsin, CFTR, surfactant (lung-specific), immunoglobulin (lymphocyte-specific), actin (muscle-specific) or SRa (hybrid between the SV40 origin and the HTLV-1 LTR; Takebe et al., 1988, Mol. Cell. Biol. 8, 466–472) genes. The promoter can also be a promoter which stimulates expression in a tumor or cancer cell. Promoters which may in particular be mentioned are the promoters of the MUC-1 gene, which is overexpressed in breast and prostate cancers (Chen et al., 1995, J. Clin. Invest. 96, 2775–2782), the CEA (standing for carcinoma embrionic antigen) gene, which is overexpressed in colon cancers (Schrewe et al., 1990, Mol. Cell. Biol. 10, 2738–2748), the tyrosinose gene, which is overexpressed in melanomas (Vile et al., 1993, Cancer Res. 53, 3860–3868), the ERB-2 gene, which is overexpressed in pancreatic cancers (Harris et al., 1994, Gene Therapy 1, 170–175), and the α-fetoprotein gene, which is overexpressed in breast and liver cancers (Kanai et al., 1997, Cancer Res. 57, 461–465). The Cytomegalovirus (CMV) early promoter is very particularly preferred.

When the expression cassette used in the present invention comprises several genes of interest, these genes can then be placed under the control of the same genetic elements (polycistronic cassette which uses an internal translation initiation site of the IRES type for reinitiating translation of the second cistron) or of independent elements.

Naturally, the cassette can also comprise additional elements which improve the expression of the gene of interest (signal sequence, nuclear localization sequence, polyadenylation sequence, IRES, tripartite leader, etc.) or its maintenance in the host cell (origin of replication, etc.). Such elements are known to the skilled person. A preferred polyadenylation sequence is derived from the SV40 virus or the rabbit β-globin gene.

A particularly advantageous embodiment involves using an adenoviral vector whose genome has been deleted for the E1, E3 and E4 regions, with an expression cassette which contains the CMV promoter, the synthetic splicing sequence isolated from plasmid pCI, the cDNA encoding human IL-2 and the SV40 virus polyA (such as pTG6215) being inserted into the genome in place of the E1 region. Another favorable variant is provided by an adenoviral vector which has a similar genome skeleton (deletion of E1, E3 and E4) and which comprises an expression cassette which is formed from the RSV promoter followed by splicing sequences comprising intron 2 of the rabbit β-globin gene, the cDNA of canine factor IX and the rabbit β-globin gene polyA (such as pTG9378). Another preferred example consists of an E1⁻E3⁻ vector into which is inserted a cassette [lacuna] the CMV promoter, the pCI synthetic intron, and the cDNA encoding human IL-2 followed by the SV40 polyA (such as pTG6624).

The invention also relates to an infectious viral particle and a eukaryotic host cell which comprises an adenoviral vector according to the invention. The said host cell is advantageously a mammalian cell, preferably a human cell, and can comprise the said vector in a form which is or is not integrated into the genome. The cell can be a primary cell or a tumor cell of hematopoietic (totipotent stem cell, leukocyte, lymphocyte, monocyte or macrophage, etc.), muscle (satellite cell, myocyte, myoblast, etc.), cardiac, hepatic, pulmonary, tracheal, epithelial or fibroblast origin. An infectious viral particle according to the invention is prepared by any technique which is conventional in the field of the art (Graham and Prevect, 1991, loc. cit). More precisely, the adenoviral vector according to the invention is propagated in a complementing cell line which is able to supply the defective functions in trans in order to produce the polypeptides which are required for constituting the infectious viral particles. Use will, in particular, be made of the cell lines which are described in the international applications WO 94/28152 and WO 97/04119. It is also possible to make use of an appropriate cell line, such as the 293 cell line for complementing the E1 function (Grahma et al, 1977, loc. cit.) or the A549-E1 cell line (WO94/28152). In the case of multiple complementation, it is also possible to employ a helper virus or a state-of-the-art complementing cell line (for example Lusky et al., 1998, J. Virol 72, 2022–2033).

The invention also relates to a process for preparing an infectious viral particle comprising an adenoviral vector according to the invention, according to which process:

(i) the said adenoviral vector according to the invention is introduced into a complementing cell which is able to complement the said vector in trans so as to obtain a transfected complementing cell, (ii) the said transfected complementing cell is cultured under conditions which are appropriate for enabling the said infectious viral particle to be produced, and (iii) the said infectious viral particle is recovered from the cell culture.

While the infectious viral particle can of course be recovered from the culture supernatant, it can also be recovered from the cells. One of the commonly employed methods consists in lyzing the cells by means of consecutive freezing/thawing cycles in order to collect the virions in the lysis supernatant. These virions can be amplified and purified using the techniques of the art (chromatographic method, ultracentrifugation, in particular through a cesium chloride gradient, etc.).

The invention also relates to a pharmaceutical composition which comprises, as a therapeutic or prophylactic agent, an adenoviral vector, an infectious viral particle or a eukaryotic host cell according to the invention in combination with a pharmaceutically acceptable excipient. The composition according to the invention is, in particular, intended for the preventive or curative treatment of genetic diseases (hemophilia, diabetes, cystic fibrosis, Duchenne's or Becker's myopathy, autoimmune diseases, etc.), of cancers and tumors, of viral diseases (hepatitis B or C, AIDS, herpetic infections, etc.), and of cardiovascular diseases (restenoses, etc.).

A pharmaceutical composition according to the invention can be manufactured in a conventional manner with a view to administering it locally, parenterally or by the digestive route. In particular, a therapeutically effective quantity of the therapeutic or prophylactic agent is combined with a pharmaceutically acceptable excipient. Numerous routes of administration can be envisaged. Examples which may be mentioned are the intragastric, subcutaneous, intracardiac, intramuscular, intravenous, intraperitoneal, intratumor, intranasal, intrapulmonary and intratracheal routes. Administration by means of aerosol or instillation is advantageous in the case of these last three embodiments. The administration can be effected as a single dose or as a dose which is repeated once or on several occasions after a particular time interval. The appropriate route of administration and dosage vary according to a variety of parameters, for example in accordance with the individual or the disease to be treated or, again, in accordance with the gene(s) of interest to be transferred. In particular, the viral particles according to the invention can be formulated in the form of doses of between $10^4$ and $10^{14}$ pfu (plaque forming units), advantageously between $10^5$ and $10^{13}$ pfu, preferably between $10^6$ and $10^{12}$ pfu. The formulation can also include a diluent, an adjuvant or an excipient which is acceptable from a pharmaceutical point of view. The formulation can be presented in liquid or dry (lyophilisate, etc.) form.

The viral particles and vector according to the invention can, where appropriate, be combined with one or more substances which improve their transfectional efficacy and/or stability. These substances are widely documented in the literature which is accessible to the skilled person (see, for example, Felgner et al., 1987, Proc. West. Pharmacol. Soc. 32, 115–121; Hodgson and Solaiman, 1996, Nature Biotechnology 14, 339–342; Remy et al., 1994, Bioconjugate Chemistry 5, 647–654). As an illustration, but not a limitation, the substances can be polymers, lipids, in particular cationic lipids, liposomes, nuclear proteins or neutral lipids. These substances can be used on their own or in combination.

Finally, the present invention relates to the use of an adenoviral vector, an infectious viral particle or a eukaryotic host cell according to the invention for transferring a gene of interest into a host cell or organism. According to a first possibility, the medicament can be administered directly in vivo (for example by intravenous injection, intramuscular injection, injection into an accessible tumor, administration to the lungs by means of an aerosol, etc.). It is also possible to adopt the ex vivo approach, which consists in removing cells from the patient (bone marrow stem cells, peripheral blood lymphocytes, etc.), transfecting or infecting them in vitro in accordance with the techniques of the art, and then readministering them to the patient. The preferred use is for preparing a medicament which is intended for treating the human or animal body by means of gene therapy.

Finally, the present invention also relates to the use of an adenoviral vector according to the invention for improving the expression of a gene of interest in a host cell or organism by a factor of at least 20, advantageously of at least 50 and preferably of at least 100. The level of improvement can easily be determined by comparing the expression of the gene of interest, in a given adenoviral context, in the presence and in the absence of the said splicing sequence.

The invention also extends to a method of treatment according to which a therapeutically effective quantity of an adenoviral vector, of a viral particle or of a eukaryotic host cell according to the invention is administered to a patient who is in need of such treatment.

FIG. 1 is a diagram of the genome of the human type 5 adenovirus (depicted in 0 to 100 arbitrary units) showing the locations of the different genes.

EXAMPLES

The present invention is illustrated, without for all that being limited, by the following examples.

The constructs which are described below are prepared in accordance with the general techniques of genetic engineering and molecular cloning, which are detailed in Maniatis et al., (1989 Laboratory Manual, Cold Spring Harbor, Laboratory Press, Cold Spring Harbor, N.Y.) or in accordance with the manufacturer's recommendations when a commercial kit is used. The homologous recombination steps are preferably carried out in the *E. coli* strain BJ 5183 (Hanahan, 1983, J. Mol. Biol. 166, 577–580). The technique employed for repairing the restriction sites consists in using the large fragment (Klenow fragment) of *E. coli* DNA polymerase I to fill in the protruding 5' ends. The PCR (Polymerase Chain Reaction) amplification techniques are known to the skilled person (see, for example, PCR Protocols—A Guide to Methods and Applications, 1990, edited by Innis, Gelfand, Sninsky and White., Academic Press Inc). Furthermore, the adenoviral-genome fragments which are employed in the different constructs described below are shown precisely in accordance with their position in the nucleotide sequence of the Ad5 genome, as disclosed in the Genebank database under reference M73260.

As regards the cell biology, the cells are transfected or transduced and cultured using the standard techniques which are well known to the skilled person. The cell lines 293 (Graham et al., 1977, loc. cit.; available from the ATCC under reference CRL1573), LCA-1 (corresponding to the clone 5606#5-38 which is described in Example 3. in application WO94/04119), A549, which is of epithelial origin and which is derived from a pulmonary carcinoma (ATCC CCL-185) and A549-E1 (Example 6 of WO94/28156) are used in the examples which follow. It is understood that other cell lines can be used. It is pointed out that the cell line A549-E1 is a cell line for complementing the adenoviral E1 function, with this cell line being obtained by transfecting a plasmid which carries the Ad5 E1 sequences (nt 505 to 4034) expressed from the PGK promoter. The stable clones which have been selected using puromycin are tested for their complementation ability and the best producer clone (#73) is selected.

Example 1

Constructing the Adenoviral Vector AdTG6215, Which Expresses the Human Interleukin 2 Gene The BglII/BamHI fragment, carrying the CMV promoter, the splicing sequence, a multiple cloning site (MCS) and the SV40 virus polyA sequence, is isolated from plasmid pCI (Promega) and inserted into a conventional plasmid. The cDNA sequences encoding human IL-2 (Taniguchi et al., 1983, Nature 302, 305–311) are isolated in the form of a XhoI/EcoRI fragment (where appropriate by PCR) and introduced into the MCS. The cassette is cloned into an adenoviral transfer vector, in place of the EI adenoviral region, in order to give pTG6601. The transfer vector contains nt 1 to 458 and 3329 to 6241 of Ad5 in a ppolyII plasmid. pTG6215 is generated by means of homologous recombination between the PacI/BstEII fragment, which is isolated from pTG6601, and the ClaI-linearized vector pTG8595 (Chartier et al., 1996, J. Virol. 70, 4805–4810). The adenoviral vector pTG6215 contains the Ad5 genome, lacking the E1 (nt 459 to 3327), E3 (nt 28,592 to 30,470) and E4 (nt 32,994 to 34,998) regions, and the "CMV promoter-pCI splicing sequence—IL-2 cDNA and SV40 pA" cassette, which has been inserted in place of the adenoviral E1 sequences.

As a control, the vector pTG6692 is generated by deleting the splicing sequences from the expression block isolated from pCI by digesting with PstI and religating. The IL-2 cDNA is cloned, and the "no intron" cassette is inserted into the adenoviral genome, as shown above.

Finally, it is useful to compare the effect of the splicing sequences in a first-generation adenoviral vector context. To do this, the vector pTG6624 is constructed by carrying out homologous recombination between the PacI-BstEII fragment, which has been isolated from pTG6601, and the ClaI-linearized vector pTG4656. This latter vector is equivalent to pTG8595 except for the fact that it carries a complete E4 region, such that the final TG6624 construct corresponds to the Ad5 genome, which is deleted for the E1 (nt 459 to 3327) and E3 (nt 28,592 to 30,470) regions, together with the "CMV promoter-pCI splicing sequence-IL-2 cDNA and SV40 pA" cassette, which is inserted in place of E1. The "no intron" first-generation vector designated pTG6229 results from deleting the splicing sequences by digesting with PstI and cloning the no-intron cassette into the adenoviral genome by means of homologous recombination with vector pTG4656.

The adenoviruses AdTG6215 and AdTG6692 are obtained by transfecting the PacI fragment, which has been isolated from the corresponding vectors, into LCAI cells using the calcium phosphate technique. The first generation virions AdTG6624 and AdTG6229 are produced in cell line 293. The viruses are isolated, propagated and purified under the customary conditions.

The human A549 cells are set to culture and then infected at confluence with the above virions while keeping to a multiplicity of infection of approximately 100. The quantities of IL-2 which are secreted into the culture supernatants which are recovered 48 h after infection are determined by ELISA (Quantikine hIL-2 kit, R&D System, Minneapolis). In a second-generation adenoviral vector context (E1$^-$, E3$^-$ and E4$^-$), the IL-2 is produced in quantities which are from 100 to 150 times higher when the virions carry an expression cassette which is provided with an intron (AdTG6215) than when they lack such an expression cassette (AdTG6692). These latter virions synthesize very low levels of IL-2 such that they cannot be considered for therapeutic use. In comparison, the amplification factor in a first generation virus context (E1$^-$, E3$^-$) is 2.5.

Example 2

Constructing the Adenoviral Vector AdTG9378, Which Expresses the Gene Encoding Canine Factor IX The recombinant cassette consisting of the RSV promoter, the splicing sequence of the second intron of the rabbit β-globin gene placed 5' of the canine FIX cDNA, followed by the polyA of the rabbit β-globin gene, is firstly reconstituted. The β-globin splicing and polyA sequences are excised from the vector pBCMGNeo (Karasuyama et al., 1989, loc. cit.) by digesting with SalI/BamHI and cloned downstream of the RSV promoter, which is carried by the SalI/BamHI fragment which is isolated from the vector pREP4 (Invitrogen V004-50). The cDNA encoding canine FIX, whose sequence is described in Evans et al. (1989, Blood 74, 207–212), is then inserted downstream of the splicing sequences. The transcription unit is placed in a transfer vector which contains the Ad5 sequences 1 to 458 and 3328 to 5778, in order to give pTG9350. The adenoviral vector pTG9378 is obtained by means of homologous recombination between the PacI/BglI fragment, isolated from pTG 9350, and the ClaI-linearized vector pTG8595 (Chartier et al., 1996, loc. cit.). It contains the Ad5 genome, lacking the E1 (nt 459 to 3327), E3 (nt 28,592 to 30,470) and E4 (nt 32,994 to 34,998) regions, and the abovementioned FIX cassette, which is inserted in place of EI.

As before, a control, designated pTG5666, is constructed whose adenoviral skeletal framework corresponds to a second-generation vector apart from the fact that the FIX cassette lacks splicing sequences, as a result of digestion with PstI.

Similarly, two first-generation vectors, pTG9370 and pTG9383, are constructed, which vectors differ by the presence or absence, respectively, of the 2β-globin intron in the FIX cassette. The first of these vectors is obtained by means of homologous recombination between the PacI/BglI fragment, isolated from pTG9350 and the ClaI-linearized vector pTG4656, which is deleted for the E1 (nt 459 to 3327) and E3 (28,592 to 30,470) regions. The second vector results from recombination between the intron-less PacI/BglI fragment and pTG4656.

The viral particles are generated by transfecting the PacI fragments of the above plasmids into the 293 (AdTG9370 and AdTG9383) or LCA1 (AdTG9378 and AdTG5666) cell lines. The viruses are isolated, propagated and purified under the customary conditions. The A549 target cells are set to culture and then, having reached confluence, are infected with the above virions while keeping to a multiplicity of infection of approximately 100. The quantities of canine FIX secreted into the culture supernatants which are recovered 48 h after infection are determined by ELISA (see, for example, Axelrod et al., 1990, Proc. Natl. Acad. Sci. USA 87, 5173–5177; Roman et al., 1992, Somat. Cell Mol. Genet. 18, 247–258; Miyanohara et al., 1992, New Biol. 4, 238–246; Lozier et al., 1994, JAMA 271, 47–51). A particularly appropriate test uses the monoclonal antibody FXCOO8 (Bajaj et al., 1985, J. Biol. Chem. 260, 11,574–11,580) as the capture antibody, at the rate of 200 ng per well, and a peroxidase-coupled rabbit antibody, which is specific for human FIX (STAGO), as the detection antibody. The secretion of canine FIX in the A549 cells infected with the second generation viruses is 20 times higher when the cassette contains splicing sequences (AdTG9378) than when it lacks these sequences (AdTG5666). When the transduction uses first-generation vectors, the beneficial effect of the intron is less marked (amplification factor of approximately 2.5).

Replacing the FIX cDNA with that encoding human IL-2 gives rise to the vector pTG6214. This vector is equivalent to AdTG9378 apart from the gene of interest.

Example 3

Effect of the Intron on Viral Production

Approximately $10^7$ A549-E1 #73 cells are set to culture in F25 flasks and are infected with the viruses AdTG6624 (ΔE1ΔE3+intron) or AdTG6229 (ΔE1ΔE3–intron) at an MOI of 1. The infection is carried out at 37° C. for 30 min in DMEM (Dulbecco's modified Eagle's medium) to which 2% serum has been added. The cultures are harvested at times 24 h, 48 h, 72 h and 96 h and the virions released from the cells by thermal shocks. The viral titer is assessed by DBP protein immunofluorescence using a specific monoclonal antibody (Reich et al., 1983, Virology 128, 480–484). The amplification factor is determined by the ratio of the number of final infectious units (i.u.) over the number of initial infectious units. An amplification factor of the order of 1900, 4100 and 3300 is observed with the two types of constructs 48, 72 and 96 h post-infection, respectively. When the same experiment is conducted in 175 flasks (MOI=3 and harvesting 3 days post-infection), the production yield (i.u//cell; is appreciably higher (by approximately 25%) using the ADTG6642 viruses which contain an expression cassette provided with an intron. Taken overall, these results indicate that the presence of the synthetic pCI intron does not have any negative effect on virus-production yields.

Example 4

Ability of the Vectors to Function in Vitro and In Vivo

Various cell types, i.e. both established cell lines of varying origin [human, simian or murine: A549, Vero and W162 (Weinberg and Ketner, 1983, Proc. Natl. Acad. Sci. USA 80, 5384–5386)] and primary cells of mouse (fibroblasts), canine (myoblasts) and, in particular, human origin [primary tumors derived from a stomach cancer (passage 5) and from a liver metastasis of a colon cancer (passage 2)] are transduced in the standard manner at an moi of from 50 to 100. The following viruses are employed: AdTG6624 (ΔE1ΔE3 pCMV+intron), AdTG6229 (ΔE1ΔE3 pCMV–intron), AdTG6215 (ΔE1ΔE3ΔE4 pCMV+intron) or AdTG6692 (ΔE1ΔE3ΔE4 pCMV–intron), AdTG6214 (ΔE1ΔE3ΔE4 pRSV+intron) and its control (ΔE1ΔE3ΔE4 pRSV–intron). The supernatants are harvested 24 and 72 h after infection and the quantities of IL-2 secreted are determined by means of ELISA, as before.

The assays indicate the beneficial effect of the intron in terms of IL-2 production, with the latter being from 2 to 3 times higher in a first-generation vector context and more than 100 times in a ΔE1ΔE3ΔE4 context. It is noted that the AdTG6624 virions produce the most IL-2, demonstrating the value in combining the CMV promoter and the synthetic intron in a first-generation vector framework.

The antineoplastic activity of the virions expressing IL-2 is evaluated in vivo in a murine tumor model. Immunodeficient female B6D2 mice aged from 6 to 8 weeks are rendered cancerous by the administration of $3 \times 10^5$ P815 tumor cells, Once the tumors have become palpable (from 3 to 4 mm in diameter), $5 \times 10^8$ infectious particles of AdTG6624 are inoculated by the intratumor route on D0, D1 and D2 and the survival of the animals over time is monitored. The percentage survival of the animals treated with the AdTG6624 viruses reaches 40% more than 40 days post-infection. By comparison, the animals treated with a control virus containing a cassette for the expression of IL-2, without any intron and directed by the MLP promoter, exhibit a much lower rate of survival.

What is claimed is:

1. A method for in vivo transferring a gene of interest into a host cell or organism comprising
introducing into said host cell or organism in vivo an adenoviral vector derived from the genome of an adenovirus at least by deleting all or part of the E1 region,
wherein said adenoviral vector contains a cassette for expressing a gene of interest;
wherein said gene of interest is placed under the control of transcriptional and translational control elements required for expressing it in a host cell or organism;
wherein said elements comprise at least one splicing sequence, which is located after the transcriptional initiation site or a promoter and before a poly A site;
wherein said splicing sequence is derived from a β-globin gene or a sequence which is homologous with, or identical to, the sequence depicted in SEQ ID NO: 1 or SEQ ID NO:2.

2. The method according to claim 1, wherein the said splicing sequence is derived from intron 2 of the rabbit β-globin gene or from a splicing sequence which comprises the splicing donor site of intron 1 of the human β-globin gene as well as the branching point and the splicing acceptor site of the gene for a mouse immunoglobin.

3. The method according to claim 1, wherein the said splicing sequence is inserted into the said expression cassette between a first exon and a second exon of the gene of interest.

4. The method according to claim 1, wherein the said splicing sequence comprises an exon sequence at one or other of its ends and is inserted into the said expression cassette 5' or 3' of the gene of interest, with the gene being of the cDNA type.

5. The method according to claim 1, wherein the adenoviral vector is also nonfunctional in at least one of the regions selected from the group consisting of E2, E4, L1, L2, L3, L4, and L5, and combination thereof.

6. The method according to claim 1, wherein the adenoviral vector additionally lacks all or part of the E3 region.

7. The method according to claim 1, wherein said adenoviral vector is selected from the group consisting of:
(1) adenoviral vector which lacks all or part of the E1 and E2 regions and, optionally, all or part of the E3 region,
(2) adenoviral vector which lacks all or part of the E1 and E4 regions and, optionally, all or part of the E3 region,
(3) adenoviral vector which lacks all or part of the E1 and E4 regions and, optionally, all or part of the E3 region, and which contains a nonfunctional mutation in the E2 region,
(4) adenoviral vector which lacks all or part of the E1, E2 and E4 regions and, optionally, all or part of the E3 region, and
(5) adenoviral vector which lacks all or part of the E1 region and, optionally, all or part of the E3 region.

8. The method according to claim 1, wherein said adenoviral vector is derived from the genome of an adenovirus of human, canine, avian, bovine, murine, ovine, porcine or simian origin or else from a hybrid which comprises adenoviral genome fragments of different origins.

9. The method according to claim 8, wherein said adenoviral vector is derived from the genome of a human type 5 adenovirus.

10. The method according to claim 1, wherein the elements which are required for expressing the said gene of interest in a host cell or organism comprise a promoter which is selected from the MLP (Major Late Promoter), PGK (Phospho Glycerate Kinase), RSV (Rous Sarcoma Virus, SRβ and CMV (Cytomegalovirus) promoters.

11. The method according to claim 1, wherein the elements which are required for expressing the said gene of interest in a host cell or organism comprise a polyadenylation sequence derived from the SV40 virus or the rabbit β-globin gene.

12. A method for in vivo transferring a gene of interest into a host cell or organism comprising introducing into said host cell or organism in vivo an infectious viral particle which comprises an adenoviral vector derived from the genome of an adenovirus at least by deleting all or part of the E1 region, wherein the adenoviral vector contains a cassette for expressing a gene of interest;

wherein the gene of interest is placed under the control of transcriptional and translational control elements required for expressing it in a host cell or organism;

wherein the elements comprise at least one splicing sequence; and wherein the splicing sequence is derived from a β-globin gene or a sequence which is homologous with, or identical to the sequence depicted in SEQ ID NO: 1 or SEQ ID NO:2.

13. A method for increasing the expression of a gene of interest by a factor of at least 20 in a host cell or organism comprising introducing into the host cell or organism an adenoviral vector derived from the genome of an adenovirus at least by deleting all or part of the E1 region, wherein the adenoviral vector contains a cassette for expressing a gene of interest;

wherein the gene of interest is placed under the control of transcriptional and translational control elements required for expressing it in a host cell or organism;

wherein the elements comprise at least one splicing sequence; and wherein the splicing sequence is derived from a β-globin gene or a sequence which is homologous with, or identical to the sequence depicted in SEQ ID NO: 1 or SEQ ID NO:2.

* * * * *

SEQUENCE LISTING

<160> NUMBER OF SEQ ID NOS: 2

<210> SEQ ID NO 1
<211> LENGTH: 250
<212> TYPE: DNA
<213> ORGANISM: synthetic splicing sequence

<400> SEQUENCE: 1

```
ctgcagaagt tggtcgtgag gcactgggca ggtaagtatc aaggttacaa g acaggttta      60 aggagaccaa tagaaactgg gcttgtcgag acagagaaga ctcttgcgtt t ctgataggc     120 acctattggt cttactgaca tccactttgc ctttctctcc acaggtgtcc a ctcccagtt     180 caattacagc tcttaaggct agagtactta atacgactca ctataggcta g cctcgaggt     240
```

```
                                             -continued cgacctgcag                                                                     250

<210> SEQ ID NO 2
<211> LENGTH: 652
<212> TYPE: DNA
<213> ORGANISM: rabbit beta globin intron 2

<400> SEQUENCE: 2
gtcgaccgat cctgagaact tcagggtgag tttggggacc cttgattgtt c tttcttttt        60 cgctattgta aaattcatgt tatatggagg gggcaaagtt ttcagggtgt t gtttagaat       120 gggaagatgt cccttgtatc accatggacc ctcatgataa ttttgtttct t tcactttct      180 actctgttga caaccattgt ctcctcttat tttcttttca ttttctgtaa c tttttcgtt      240 aaactttagc ttgcatttgt aacgaatttt taaattcact tttgtttatt t gtcagattg      300 taagtacttt ctctaatcac tttttttttca aggcaatcag ggtatattat a ttgtacttc     360 agcacagttt tagagaacaa ttgttataat taaatgataa ggtagaatat t tctgcatat      420 aaattctggc tggcgtggaa atattcttat tggtagaaac aactacaccc t ggtcatcat      480 cctgcctttc tctttatggt tacaatgata tacactgttt gagatgagga t aaaatactc     540 tgagtccaaa ccgggcccct ctgctaacca tgttcatgcc ttcttctctt t cctacagct    600 cctgggcaac gtgctggttg ttgtgctgtc tcatcatttt ggcaaagaat t c             652
```